United States Patent
Devin-Baudoin et al.

(10) Patent No.: US 6,916,467 B2
(45) Date of Patent: Jul. 12, 2005

(54) PROCESS FOR PERMANENTLY RESHAPING THE HAIR USING PARTICULAR AMINOSILICONES

(75) Inventors: Priscille Devin-Baudoin, Vanves (FR); Anne Sabbagh, Rueil Malmaison (FR)

(73) Assignee: L'Oreal S.A. (FR)

(*) Notice: Subject to any disclaimer, the term of this patent is extended or adjusted under 35 U.S.C. 154(b) by 54 days.

(21) Appl. No.: 10/290,148

(22) Filed: Nov. 8, 2002

(65) Prior Publication Data

US 2003/0115685 A1 Jun. 26, 2003

(30) Foreign Application Priority Data

Nov. 8, 2001 (FR) ............................................. 01 14479

(51) Int. Cl.$^7$ ................................................ A61K 7/09
(52) U.S. Cl. .................... 424/70.1; 424/70.2; 424/70.5; 424/70.12; 424/70.19; 424/70.122
(58) Field of Search ................................ 424/70.1, 70.2, 424/70.5, 70.12, 70.19, 70.122, 70.6

(56) References Cited

U.S. PATENT DOCUMENTS

| | | | | |
|---|---|---|---|---|
| 4,770,873 | A | * 9/1988 | Wolfram et al. | ........... 424/70.2 |
| 5,106,612 | A | 4/1992 | Maignan et al. | .............. 424/72 |
| 5,154,918 | A | 10/1992 | Maignan et al. | .............. 424/72 |
| 5,340,367 | A | 8/1994 | Schultz et al. | ................. 8/432 |
| 5,583,257 | A | 12/1996 | Junino et al. | ............... 564/154 |
| 5,925,341 | A | * 7/1999 | Cervantes et al. | ........ 424/78.03 |
| 6,177,090 | B1 | 1/2001 | Dubief et al. | ............... 424/401 |
| 6,214,326 | B1 | 4/2001 | Dupuis | ....................... 424/70.1 |
| 6,254,646 | B1 | 7/2001 | Di La Mettrie et al. | ........ 8/406 |
| 2002/0006389 | A1 | 1/2002 | Restle et al. | ............... 424/70.1 |
| 2002/0187117 | A1 | 12/2002 | Devin-Baudoin et al. | .. 424/70.2 |

FOREIGN PATENT DOCUMENTS

| | | |
|---|---|---|
| EP | 0 354 835 | 2/1990 |
| EP | 0 368 763 | 5/1990 |
| EP | 0 465 342 | 1/1992 |
| EP | 0 514 282 | 11/1992 |
| EP | 0 890 355 | 1/1999 |
| EP | 0 974 335 | 1/2000 |
| FR | 2 679 558 | 1/1993 |
| GB | 2 141 454 | 12/1984 |
| JP | 4-154713 A | 5/1992 |
| JP | 8-157340 A | 6/1996 |
| JP | 9-151120 A | 6/1997 |
| JP | 10-511698 A | 11/1998 |
| JP | 2000-007535 A | 1/2000 |
| JP | 2000-507984 A | 6/2000 |
| JP | 2001-10936 A | 1/2001 |
| JP | 2002-308742 A | 10/2002 |

OTHER PUBLICATIONS

English language Derwent Abstract of EP 0 368 763, May 16, 1990.
English language Derwent Abstract of FR 2 679 558, Jan. 29, 1993.
English language Derwent abstract of JP 4–154713 A, May 27, 1992.
English language Derwent abstract of JP 8–157340 A, Jun. 18, 1996.
English language Derwent abstract of JP 9–151120 A, Jun. 10, 1997.
English language Derwent abstract of JP 2001–10936 A, Jan. 16, 2001.

\* cited by examiner

*Primary Examiner*—Margaret Einsmann
*Assistant Examiner*—Eisa Elhilo
(74) *Attorney, Agent, or Firm*—Finnegan, Henderson, Farabow, Garrett & Dunner, L.L.P.

(57) ABSTRACT

A process for permanently reshaping keratin fibres, comprising the application to the keratin fibres, before reducing and/or after fixing, of a pre-treatment and/or post-treatment cosmetic composition comprising, in a cosmetically acceptable medium, at least one aminosilicone comprising at least one aminoethylimino($C_4$–$C_8$)alkyl group.

10 Claims, No Drawings

PROCESS FOR PERMANENTLY RESHAPING THE HAIR USING PARTICULAR AMINOSILICONES

The present disclosure relates to a process for permanently reshaping keratin fibres, for example, hair. This process may be used, for example, in professional hairstyling salons, or privately via the marketing of kits.

The expression "permanent reshaping process" means any long-lasting process for shaping, curling, straightening or relaxing the hair.

The expression "keratin fibres" means, for example, hair, eyelashes and eyebrows.

One technique for obtaining a permanent reshaping of the hair comprises, in a first stage, opening the keratin —S—S— disulphide (cystine) bonds using a reducing composition comprising a reducing agent (reduction), followed, for example, after having rinsed the hair thus treated, by reconstituting, in a second stage, the disulphide bonds by applying to the hair, which has been placed under tension beforehand (for example, with curlers and the like), an oxidizing composition (oxidizing, also known as fixing) so as to finally give the hair the desired shape. This technique thus can make it equally possible either to make the hair wavy or to straighten or relax it. The new shape given to the hair by a chemical treatment such as above can be long-lasting and may, for example, withstand the action of washing with water and/or shampoos, as opposed to other techniques for temporary reshaping, such as hairsetting.

The reducing composition that may be used to carry out the reduction of a permanent-waving process may comprise, as reducing agents, sulphites, bisulphites or thiols. Among the thiols that may be mentioned are cysteine and its various derivatives, cysteamine and its derivatives, thiolactic acid, thioglycolic acid and its esters, such as glyceryl monothioglycolate, and thioglycerol.

As to the oxidizing composition used to carry out the fixing, compositions based on aqueous hydrogen peroxide solution or alkali metal bromates may be used.

One disadvantage of the permanent-waving techniques known to date is that applying them repeatedly to the hair may induce in the long term a gradual deterioration in the quality of the hair, for example, a gradual and pronounced deterioration in the sheen and the cosmetic properties of the hair, such as the softness of the fibres, which may have a tendency to become more and more coarse, and also as regards their disentangling, the hair may become more and more difficult to disentangle. This deterioration may be pronounced when the fixing of the permanent-waving process is carried out using a bromate.

To limit this deterioration of the hair, it has already been proposed to introduce conditioners directly into the reducing composition. For example, Japanese patent applications H2-250814 and H9-151120 describe reducing compositions containing aminosilicones, which may optionally be in the form of a microemulsion.

However, processes for permanently reshaping the hair using such compositions are not entirely satisfactory, since the degree, the quality and liveliness of the curls may be insufficient and short-lived, for example, if the conditioner, such as aminosilicones, directly combined with the reducing agent to block the activity of the reducing agent.

The present disclosure addresses at least one of these disadvantages by providing a process for permanently reshaping keratin fibres, such as hair, which can reduce the degree of mechanical and/or cosmetic degradation of the hair, while at the same time providing a satisfactory degree, quality and liveliness of curls.

The inventors have discovered, surprisingly and unexpectedly, that by applying to the hair, before applying the reducing composition and/or after having applied the oxidizing composition, at least one pre-treatment and/or post-treatment cosmetic composition comprising at least one aminosilicone as defined below, it is possible to solve at least one of these problems.

One new embodiment is a process for permanently reshaping keratin fibres, such as hair, comprising the following:

(i) applying a reducing composition to the keratin fibres; and (ii) oxidizing the keratin fibres, wherein the process also comprises applying to the keratin fibres, before (i) and/or after (ii), a pre-treatment and/or post-treatment cosmetic composition comprising, in a cosmetically acceptable medium, at least one aminosilicone comprising at least one aminoethylimino($C_4$–$C_8$)alkyl group. Another embodiment relates to a pre-treatment and/or post-treatment cosmetic composition for pre-treatment and/or post-treatment in permanent reshaping of keratin fibres comprising, in a cosmetically acceptable medium in said composition, at least one aminosilicone comprising at least one aminoethylimino($C_4$–$C_8$)alkyl group.

Another new embodiment relates to a kit for permanently reshaping keratin fibres, comprising at least one compartment comprising a pre-treatment and/or post-treatment cosmetic composition comprising at least one aminosilicone comprising at least one aminoethylimino($C_4$–$C_8$)alkyl group.

In one new embodiment, the at least one aminosilicone is of the following formula:

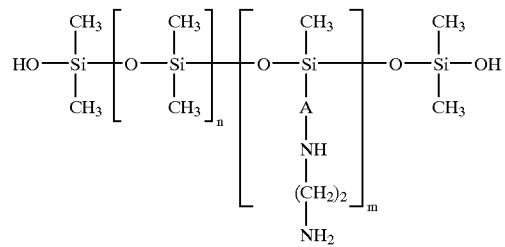

in which:

A is chosen from linear and branched $C_4$–$C_8$ alkylene radicals, for example, linear and branched $C_4$ alkylene radicals;

m and n are numbers such that the sum (n+m) may range from 1 to 2 000, such as from 50 to 150; n is a number, for example, ranging from 0 to 1 999, further for example, from 49 to 149; and m is a number, for example, ranging from 1 to 2 000, further for example, from 1 to 10.

The viscosity of the at least one aminosilicone may be, for example, greater than 25 000 mm²/s at 25° C.

Further, for example, this viscosity may range from 30 000 to 200 000 mm²/s at 25° C., such as from 30 000 to 150 000 mm²/s at 25° C.

The viscosity is measured at 25° C. according to ASTM standard 445, Appendix C.

The at least one aminosilicone has a weight-average molecular mass ranging, for example, from 2 000 to 1 000 000, and further, for example, from 3 500 to 200 000.

The weight-average molecular mass of the at least one aminosilicone is measured by Gel Permeation Chromatography (GPC) at room temperature as polystyrene equivalent. The columns used are μ styragel columns. The eluent is THF, the flow rate is 1 ml/min. 200 µl of a solution containing 0.5% by weight of silicone in THF are injected. The detection is made by refractometry and UVmetry.

The at least one aminosilicone may be used as is or in the form of emulsions. The emulsion may comprise at least one surfactant. The at least one surfactant may be of any type, such as cationic and/or nonionic. The mean particle size of the at least one aminosilicone in the emulsion ranges, for example, from 3 nm to 500 nm, further, for example, from 70 nm to 500 nm, and even further, for example, from 150 to 275 nm. One of ordinary skill in the art can measure such particle sizes by known techniques. Such particle sizes are measured with a laser granulometer.

An example of the aminosilicone corresponding to this formula is DC2-8299® from Dow Corning.

In one embodiment, the concentration of the at least one aminosilicone comprising at least one aminoethylimino ($C_4$–$C_8$)alkyl group in the pre-treatment and/or post-treatment composition ranges, for example, from 0.05 to 10% by weight relative to the total weight of the composition, such as from 0.1 to 7% by weight relative to the total weight of the composition.

The pre-treatment and/or post-treatment composition comprising at least one aminosilicone as defined above may further comprise at least one active agent chosen from water-soluble and liposoluble active agents, having cosmetic and/or dermopharmaceutical activity. Non-limiting examples of those active agents include vitamins and derivatives thereof such as vitamin E, vitamin E acetate, vitamin C and its esters, the B vitamins, vitamin A alcohol and retinol, vitamin A acid and retinoic acid and its derivatives, provitamins such as panthenol, vitamin A palmitate, niacinamide, ergocalciferol, antioxidants, essential oils, wetting agents, silicone and non-silicone sunscreens, preserving agents, sequestering agents, pearlescent agents, pigments, moisturizers, antidandruff agents, anti-seborrhoeic agents, plasticizers, hydroxy acids, electrolytes, solvents and fragrances.

The compositions may also comprise at least one solvent such as C1–C8 lower alcohols such as ethanol.

The pH of the pre-treatment and/or post-treatment composition comprising at least one aminosilicone as defined above ranges, for example, from 2 to 10, such as from 3 to 9.

In one embodiment, the pre-treatment composition comprising at least one aminosilicone as defined above is applied to the hair to be treated, which may optionally have been moistened beforehand. This application may be performed after the usual procedure of placing the hair under tension in a shape corresponding to the desired final shape of the hair (for example, curls). This procedure itself can possibly be carried out by any implements, such as a mechanical implement, that is suitable and known per se for maintaining hair under tension, such as, rollers, curlers and the like.

In another embodiment, the pre-treatment and/or post-treatment composition comprising at least one aminosilicone as defined above is left to act on the hair, at room temperature or under heat, for a period of time ranging from, for example, 1 to 60 minutes, such as from 3 to 30 minutes.

According to an option in the process, the hair impregnated with the pre-treatment composition comprising at least one aminosilicone as defined above can be rinsed, wherein the rinsing may be carried out using water.

In the process, a reducing composition is applied to the hair, wherein the reducing composition may comprise at least one thiol.

The thiol in the reducing composition may be chosen from thiols known as reducing agents such as thioglycolic acid, glyceryl and glycol monothioglycolate, cysteamine and its $C_1$–$C_4$ acyl derivatives such as N-acetylcysteamine or N-propionyl-cysteamine, cysteine, N-acetylcysteine, sugar N-mercaptoalkylamides such as N-(2-mercaptoethyl) gluconamide, 3-mercaptopropionic acid and its derivatives, thiolactic acid and its esters such as glyceryl monothiolactate, thiomalic acid, pantethine, thioglycerol, alkali metal and alkaline-earth metal sulphites and bisulphites, the N-(mercaptoalkyl)-ω-hydroxyalkylamides described in patent application EP-A-354 835 and the N-mono- or N,N-dialkylmercapto-4-butyramides described in patent application EP-A-368 763, the aminomercaptoalkylamides described in patent application EP-A-432 000, the N-(mercaptoalkyl)succinamic acid and N-(mercaptoalkyl)succinimide derivatives described in patent application EP-A-465 342, the alkylaminomercaptoalkylamides described in patent application EP-A-514 282, and the mixture of 2-hydroxypropyl thioglycolate and of 2-hydroxy-1-methylethyl thioglycolate described in patent application FR-A-2 679 448.

In one embodiment, thioglycolic acid, thiolactic acid and 3-mercaptopropionic acid are chosen for use.

The reducing agents may be present in a concentration that may range, for example, from 1% to 20% by weight relative to the total weight of the reducing composition.

The pH of the reducing composition may range, for example, from 6 to 10, and further, for example, from 7 to 9.

The pH values of the reducing compositions may be conventionally adjusted by adding at least one basifying agent. Non-limiting examples of such basifying agents include, for example, aqueous ammonia, monoethanolamine, diethanolamine, triethanolamine, isopropanolamine, 1,3-propanediamine, ammonium and alkali metal carbonates and bicarbonates, primary, secondary and tertiary amine carbonates and bicarbonates and organic carbonates such as guanidine carbonate.

The reducing composition may be in the form of a thickened or unthickened lotion, a cream, a gel, or any other suitable form, and may comprise additives known for their use in reducing compositions for permanently reshaping the hair.

The reducing composition may also be of the exothermic type, i.e., the type causing a certain level of heating during application to the hair, affording a pleasant sensation to the person on whom the permanent-waving or straightening process is being performed.

The reducing composition may also comprise a solvent such as, ethanol, propanol, isopropanol and glycerol, in a maximum concentration of 20% by weight relative to the total weight of the composition.

When the compositions are intended for a hair straightening or relaxing process, the reducing composition may be, for example, in the form of a thickened cream so as to keep the hair as straight as possible. These creams are prepared in the form of "heavy" emulsions, for example based on glyceryl stearate, glycol stearate, self-emulsifiable waxes, fatty alcohols, etc.

It is also possible to use liquids or gels containing thickeners such as carboxyvinyl polymers or copolymers, which can "stick" the hairs together and keep them in the smooth position during the exposure time.

The compositions may also be in a "self-neutralizing" or "self-regulated" form and, in this case, the reducing agents used may be combined with at least one disulphide known for its use in a reducing composition for self-neutralizing permanent waving.

In one non-limiting example, the hair onto which the reducing composition has been applied is left to rest for a few minutes, such as ranging from 2 to 40 minutes, and further such as from 5 to 30 minutes, so as to allow the reducing agent sufficient time to act correctly on the hair. This waiting stage may be carried out by leaving the treated hair to rest in the open air (at room temperature or with heating). During this waiting stage, care may be taken to ensure that the hair does not dry out completely but instead remains humid.

The hair impregnated with the reducing composition can then be carefully rinsed, for example, with water. Optionally, after rinsing, a heating at high temperature for a few seconds may be carried out.

An oxidizing composition can then be applied to the hair thus rinsed, with the aim of fixing the new shape given to the hair. It may also be envisaged to leave the hair to be oxidized by the air.

The oxidizing composition comprises an oxidizing agent that may be chosen from aqueous hydrogen peroxide solution, alkali metal bromates, persalts and polythionates. As mentioned previously, one of the advantages of an embodiment of the process disclosed is that it can be entirely suitable in the case of bromate-based oxidizing compositions. The bromate concentration in the oxidizing composition ranges, for example, from 0.1 to 2 M.

The pH of the oxidizing composition may range, for example, from 2 to 10.

As in the case of the application of the reducing composition, the hair onto which the oxidizing composition has been applied is then left for a standing or waiting stage that may last a few minutes, for example, ranging from 3 to 30 minutes and further, for example, from 5 to 15 minutes.

The post-treatment composition comprising at least one aminosilicone as defined above is, for example, applied, after rinsing out the oxidizing composition, to wet or dry hair. The hair that has undergone the post-treatment may optionally be dried and/or heated and/or rinsed, before being styled. Where appropriate, the composition may be applied while the hair is maintained by a mechanical device, for example, hairsetting rollers or curlers.

Usually, the hair impregnated with the oxidizing composition is rinsed carefully, such as with water. Before or after rinsing, the keratin fibres may be separated from the implement used for placing the keratin fibres under tension.

The hair finally obtained can have good cosmetic properties: the hair can be shinier, softer and easier to disentangle or to style.

In one embodiment, the pre-treatment and/or post-treatment composition comprising at least one aminosilicone as defined above is applied according to at least one of the following variants:

to clean, wet hair, before using the implement for placing the hair under tension, without rinsing the hair before applying the reducing agent; and to wet hair after rinsing out the fixing agent, the hair being subsequently either rinsed and/or dried.

When the process for permanently reshaping the hair is a straightening process, it is possible, in a manner that is known per se, to use a straightening agent, such as a thiol agent or an alkaline agent.

In the case of a thiol straightening agent, the process may be carried out, for example, by applying the pre-treatment and/or post-treatment composition comprising at least one aminosilicone as defined above according to at least one of the following variants:

to clean, wet hair, without rinsing before applying the reducing agent; and to clean, wet hair, after rinsing out the fixing agent, by rinsing before drying the hair.

In the case of an alkaline straightening agent, the process may be carried out, for example, by applying the pre-treatment and/or post-treatment composition comprising at least one aminosilicone as defined above to wet hair, after rinsing out neutralizing shampoo, by rinsing before drying the hair.

In the case of a hair curling process, the process may give lively curls, and the hair may be at least one of supple, light, silky and well separated.

In the case of a hair straightening process, the process, for example, may afford control of the body of the hair, may make the hair smooth from the root to the tip, and may give a more natural feel.

The present disclosure may be understood more clearly with the aid of the non-limiting examples which follow, which constitute various embodiments of the process.

In the examples, the term "am" means active material.

EXAMPLES

1) Protective Care Composition Before Permanent-waving

| Ingredients | % am |
| --- | --- |
| cetylstearyl alcohol/sodium lauryl sulphate/cetyl myristate/myristyl alcohol (62/20/8/10) | 12 |
| oxyethylenated oleyl alcohol (20 EO) | 0.1 |
| glycerine | 0.5 |
| PDMS containing aminoethylaminobutyl-α, ω-disilanol in cationic emulsion (DC2-8299 from Dow Corning) | 2 |
| demineralized water | qs 100 g |

2) Care Composition for Straightened and Permanent-waved Hair

The composition described in 1) may be used for the care of recently straightened or permanently-waved hair. This composition was applied to wet hair after rinsing out the neutralizing shampoo, or after rinsing out the fixing agent in the case of permanent waving. This composition can make the hair smooth and soft.

What is claimed is:

1. A process for permanently reshaping keratin fibres, comprising:

(i) applying a reducing composition to the keratin fibres; and (ii) oxidizing the keratin fibres, wherein the process further comprises applying to the keratin fibres, before (i) and/or after (ii), a pre-treatment and/or post-treatment cosmetic composition comprising, in a cosmetically acceptable medium, at least one aminosilicone of the following formula:

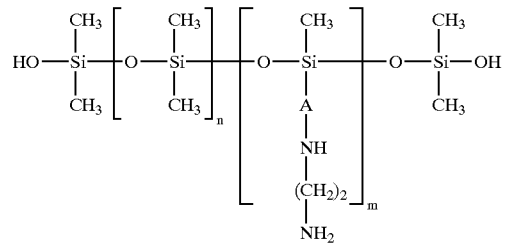

in which:

A is chosen from linear and branched $C_4$–$C_8$ alkylene radicals;

m and n are numbers such that the sum (n+m) ranges from 1 to 2000, n is a number ranging from 0 to 1999, and m is a number ranging from 1 to 2000.

2. The process according to claim 1, wherein A is chosen from linear and branched $C_4$ alkylene radicals.

3. The process according to claim 1, wherein the sum (n+m) ranges from 50 to 150.

4. The process according to claim 1, wherein n is a number ranging from 49 to 149.

5. The process according to claim 1, wherein m is a number ranging from 1 to 10.

6. The process according to claim 1, wherein the viscosity of the at least one aminosilicone is greater than 25 000 $mm^2/s$ at 25° C.

7. The process according to claim 6, wherein the viscosity of the at least one aminosilicone ranges from 30 000 to 200 000 $mm^2/s$ at 25° C.

8. The process according to claim 7, wherein the viscosity of the at least one aminosilicone ranges from 30 000 to 150 000 $mm^2/s$ at 25° C.

9. The process according to claim 1, wherein the pre-treatment and/or post-treatment composition further comprises vitamins and derivatives thereof chosen from vitamin E, vitamin E acetate, vitamin C and its esters, B vitamins, vitamin A alcohol and retinol, and vitamin A acid and retinoic acid and derivatives thereof.

10. The process according to claim 1, wherein the pre-treatment and/or post-treatment composition further comprises provitamins chosen from panthenol, vitamin A palmitate, niacinamide, and ergocalciferol.

* * * * *